United States Patent [19]
Kreutz

[11] Patent Number: 5,985,927
[45] Date of Patent: Nov. 16, 1999

[54] MEDICAMENTS FOR THE SELECTIVE TREATMENT OF TUMOR TISSUES

[76] Inventor: Werner Kreutz, Am Schlossberg, D-79219 Staufen, Germany

[21] Appl. No.: 08/930,488

[22] PCT Filed: Mar. 22, 1996

[86] PCT No.: PCT/DE96/00539

§ 371 Date: Feb. 17, 1998

§ 102(e) Date: Feb. 17, 1998

[87] PCT Pub. No.: WO96/30003

PCT Pub. Date: Oct. 3, 1996

[30] Foreign Application Priority Data

Mar. 30, 1995 [DE] Germany .......................... 195 11 623

[51] Int. Cl.⁶ .......................... A01N 37/10; A01N 37/12; C07C 65/01; C07C 229/60
[52] U.S. Cl. .......................... 514/568; 514/546; 514/548; 514/567; 560/130; 560/142; 560/143; 560/144; 560/146; 562/453; 562/472; 562/475; 568/771
[58] Field of Search .......................... 568/771; 562/453, 562/475, 472; 514/567, 568, 546, 548; 560/130, 142, 143, 144, 146

[56] References Cited

U.S. PATENT DOCUMENTS 3,914,324 10/1975 Maggioni ............................... 568/771
4,724,234 2/1988 Cone, Jr. .

FOREIGN PATENT DOCUMENTS 80 00791 5/1980 WIPO .
94 27584 12/1994 WIPO .
95 24897 9/1995 WIPO .

OTHER PUBLICATIONS

Database CANCERLIT on STN, AN No. 91295953, Gichner et al., 'UV–irradiation potentiates the antimutagenicity of p–aminobenzoic and p–aminosalicylic acids in salmonella typhimurium.' Mutatuion Research (1991), vol. 249, No. 1, pp. 119–23. abstract.
Database CANCERLIT on STN, AN No. 93235596, Zhang et al., 'Synthesis, antiinflammaory and anticancer activity of cinnamic acids, and their derivatives and analogues.' YAo Hsueh Hsueh Pao [Acta Pharmaceutica Sinica] (1992), vol. 27, No. 11, pp. 817–823. abstract.
Databas CAPLUS on STN, AN No. 1970:76945, Eisen et al., 'Myeloma proteins with antihapten antigody activity.' Fed. Proc., Fed. Amer. Soc. Exp. Biol. (1970), 29(19), pp. 78–84. abstract.
Database CAPLUS on STN, No. 71:20684, Murakami et al., 'Antitumor activity of catechol and its reaction with deoxyrivonucleic acid.' abstract of Kyushu Daigaku Nogakubu Gakugei Zasshi (1969), 24(1), 13–17.

Database CAPLUS on STN, Nol 67:8669, Bohm et al., 'Phenolic compunds in ferns. I. A survey of some ferns for cinnamic acid and benzoic acid derivatives.' abstract of Can. J. Bot. (1967), 45(5), 585–93.
Database CAPLUS on STN, No. 86:37254, Guseinov et al., 'Extraction–spectrophotometric study of the complesing of silver(I) with o–nitrobenzeneazopyrocathechuic acid and o–phenanthroline.' abstract of Uch. Zap. Azerv. Un–t. Ser. Khim. N. (1975), (3–4), 25–3.
Chem. Pharm. Bull., 32(3), 1135–1141 (1984), S. Inayama et al, "Studies on Non–Sequiterpenoid Constituents . . . ".
Trop. Med. and Int'l. Health, 1(3), 379–384 (Jun. 1996), P.M. Loiseau, et al "Plasmodium Berghei Mouse Model . . . ".
Fitoterapia, 66(5), 399–402, J. Ulrichova, et al, "Cytoprotective Effect of Phenolics . . . ".
Eur. J. Pharmacol., 201(1) 53–58 M. Trautmann, et al, "Aspirin–Like Drugs, Ethanol–Induced . . . ".
Cancer Research, 53, 806–809, Feb. 15, 1993, M.S. Anderson, et al, "Enhancement of Merocyanine . . . ".
Tumor Biol., 15, 304–310 (1994), T. Severin, et al, pH–Dependent LAK Cell Cytotoxicity.
Dialog(R) File 399: CA Search (R), Sokolik, J., et al, "Anti–Inflammatory and Antipyretic Activities . . . ".
Merck INdex, 11th Edition, (1989) p. 78.

*Primary Examiner*—Gary Geist
*Assistant Examiner*—Brian J. Davis
*Attorney, Agent, or Firm*—Michael N. Meller; Eugene Lieberstein

[57] ABSTRACT

Medicinal products for the selective control of tumor tissue and a method for control of such tumor tissue by administration of such product to a host. The products comprise: (a) two different compounds having a pH below 7 when the compounds are present in a protonated form, such compounds having the formula set forth below and (b) a pharmaceutically acceptable inert medicinal product carrier. The compounds have the following

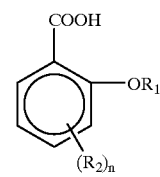

wherein $R_1$ is hydrogen or a moiety which completes an ester group or an ether group, $R_2$ is independently selected from the group consisting of an amino group, hydroxyl, an ester group, an ether group and a halogen, and n is an integer of 1 to 4.

21 Claims, 7 Drawing Sheets

MEDICAMENTS FOR THE SELECTIVE TREATMENT OF TUMOR TISSUES

BACKGROUND OF THE INVENTION

1. Field of the Invention

The invention relates to novel medicinal substances which selectively control tumor tissue, while healthy tissue is virtually not attacked. The novel medicinal substances are therefore outstandingly suitable for cancer therapy.

2. Background Art

Prior art medicines used in chemotherapy are, as a rule, only partly successful, i.e. they do not result in a definitive cure. In addition, the substances used in the prior art frequently act only on a particular category of tumors. Another disadvantage of the chemotherapeutic agents currently known are their frequently harmful side effects, because chemotherapeutic agents are generally able to have cytostatic effects on proliferating tissue. The known chemotherapeutic agents are also unsatisfactory in controlling metastasis formation, and this is one of the main reasons which has prevented decisive success in cancer therapy to date.

It is known that tumor tissue has, in the extracellular media, a reduced average pH of about 6.5 to 7.0, and the pH on the surface of cancer cells may even fall to 5, whereas the pH in normal tissue and in blood is about 7.2 to 7.5, and this is described, for example, in DE-A 44 07 484 and in Tumor Biol., 1994, 15: 304–310. These publications disclose that the natural immune defenses are blocked by the reduction in the pH range in tumor cells, because the body's own defense cells react with full cytotoxicity for cancer target cells only in the slightly basic media of more than 7. DE-A 44 07 484 therefore proposes bringing the acidic external media of cancer cells to the normal physiological pH level of 7 to 7.5 and thus controlling the cancer cells by the body's own immune defenses. To this end, the acidic external media of cancer cells is brought to a physiological pH of 7 to 7.5 either by artificial alkalinization measures or by preventing the acidification process itself.

Although the medicinal products described in DE-A 44 07 484 represent an advance in cancer therapy, it would be desirable to have available medicinal products which, besides the body's own immune defenses, selectively control tumor cells and thus can be used as chemotherapeutic agents with relatively few side effects.

OBJECT OF THE INVENTION

It is therefore an object of the present invention to provide medicinal substances which have a strong cytotoxic effect substantially selectively on tumor tissue. This object is achieved by the subject-matter of the claims.

Whereas in DE-A 44 07 484 it was attempted to increase the extracellular pH of tumor tissue and thus to destroy the tumor tissue by means of the body's own defensive substances, a different route is followed in the present instance. The intention is precisely not to alter the extracellular media in the tumor tissue in respect of the pH; on the contrary, the intention is for the reduced pH in the extracellular tumor tissue to serve as target area for substances which are pH-sensitive, i.e. either for substances which are protonated in the acidic media and act to destroy cells exclusively in this protonated state, or for substance complexes which decompose in the acidic media and thereby release a substance which acts to destroy cells. Such substances and substance complexes are activated, by reason of their pH-sensitivity, only in cancerous tumors and areas of metastasis and therefore represent an ideal cancer therapeutic agent. It should also be particularly emphasized that this novel cancer therapeutic agent acts generally on all tumor types, irrespective of the specific type of cancer.

Preferred compounds according to the invention are those which, after they have been protonated, act to destroy cells. The invention is described further on the basis of such compounds, but the following description also applies analogously to compound complexes which decompose in the acidic media of the tumor cell tissue and thereby release a substance which destroys cells.

SUMMARY OF THE INVENTION

The invention relates to a medicinal product for the selective control of tumor tissue and a method for control of such tumor tissue by administration of such product to a host. The product comprises (a) two different compounds having a pH below 7 when the product is present in a protonated form, such compounds having the formula set forth below and (b) a pharmaceutically acceptable inert medicinal product carrier.

DETAILED DESCRIPTION OF THE INVENTION

The protonated compounds may act in a variety of ways. Thus, the compounds may, after protonation has taken place, permeate reversibly through the tumor cell membrane and in this way, as proton carrier, break down the proton gradient across the tumor cell membrane. The resulting effect is an increase in the extracellular pH and a reduction in the pH in the interior of the cells, which may lead to death of the cancer cell. A side effect which occurs is that such substances, besides their harmful effect on the cancer cell, induce the natural immune defense reaction, due to the increase in the pH in the external media, as described in DE-A 44 07 484. It is also possible to use compounds which do not migrate through the membrane from the aqueous external phase of the membrane into the aqueous internal phase, but substances which are incorporated into the membrane and make proton transfer through the membrane possible. Such compounds form a defined pore for protons, i.e. they permit free or only slightly restricted diffusion of protons in the direction of their concentration gradient.

Compounds which are likewise useful are those which, in protonated form, are pore formers and which act cation-, anion- or cell substrate-specifically. Possible examples in this connection are pores for $Na^+$, $K^+$, $Cl^-$, amino acids or sugars.

However, it is particularly preferred according to the invention for the compounds to have, after their protonation in the acidic media, toxic properties and to act as cytotoxins.

Compounds preferred according to the invention for use as medicinal substance have moieties which are protonated at a pH of less than 7, preferably less than 6.5, and are toxic for cancer cells in this protonated state. The protonation preferably takes place at a pH of more than 5, particularly preferably of more than 6. The compounds preferably display a dissociation equilibrium in order to ensure reversible protonation at the required pH. The compounds according to the invention must additionally be physiologically tolerated in the range of effective concentrations, the toxicity limit preferably being between 200 mg/kg of bodyweight/day to 400 mg/kg of bodyweight/day. The compounds according to the invention for use as medicinal substance should have a suitable solubility in water, which is preferably at least approximately 20 mg/ml, particularly preferably at least 30 mg/ml.

A skilled person is able to find, with the aid of the above information and using his general expert knowledge and a few simple tests, as described hereinafter, compounds which are used according to the invention as medicinal substance. Thus, the toxicity properties of a substance which comes under consideration can be determined experimentally by the FACScan and the XTT-ELISA techniques. Both methods are known in the prior art. It is possible to investigate suspended cancer cell lines such as, for example, K-562, Raji or Daudi by both techniques, but adherent cancer cell lines only by the XTT-ELISA technique. FACS and XTT techniques can likewise be used to investigate the toxicity of the substances for mononuclear blood cells (MNCs). The proportion of dead cells is detected in the FACS technique by propidium iodide staining, and in the XTT method by conversion of XTT into formazan by mitochondrial dehydrogenase. The methods are described, for example, in Tumor-Biologie 1994, 15, 304 and in the biochemistry catalog of Boehringer Mannheim, Germany 0392.C 73.3.1465554 1 CB, Cat. No. 1465 015.

To detect pH-sensitive toxic substances, selected substances are allowed to act at various predetermined pH values, for example at pH 5.5, 6.0, 6.5, 7.0 and 7.5, both on tumor cell lines and on MNCs, for example for 4 hours and 24 hours, in order thereafter to measure the number of killed cancer cells or MNCs. Control measurements without addition of pH-sensitive substances are carried out in parallel with this. Substances are suitable for therapeutic purposes when they have toxic effects on cancer cells according to the pH characteristics and have only little, or no, toxicity on MNCs and erythrocytes in the pH range from pH>7. The skilled person is able to find, using these in vitro measurements on cell lines under defined experimental conditions and with the aid of his general expert knowledge, compounds suitable according to the invention for controlling cancer cells.

It should be noted that each type of tumor has an intrinsic average intercellular pH which is, for example, about 6.7 in the case of breast tumors and about 6.9 in the case of colonic tumors. In order to avoid the need to carry out the therapy in the direct vicinity of the physiological pH, and thus endangering normal cells and blood cells under some circumstances, the pH values in the extracellular tumor tissue can be reduced by about 0.5 pH units by inducing acidoses by glucose administration.

Examples of compounds suitable according to the invention are compounds with an aromatic system and a conjugatively coupled carboxyl, hydroxyl, sulfo and/or amino group. The aromatic system is preferably a phenyl or naphthyl group or a heteroaromatic system with 5 to 10 atoms, in which case preferably 1 or 2 atoms represent heteroatoms, preferably nitrogen or oxygen atoms. Pyridine may be mentioned by way of example. The aromatic system is particularly preferably a phenyl group.

The aromatic system has substituents which, through their inductive or mesomeric effect, alter the dissociation constant of the carboxyl, amino, sulfo or hydroxyl group in a suitable way so that protonation or deprotonation takes place in the required pH range. How to raise or lower the dissociation constant by suitable substitution of an aromatic system is known and can be found in general textbooks of organic chemistry. chemistry.

Salicylic acid and acetylsalicylic acid are not preferred according to the invention.

Suitable compounds then have the structure where ⊙ denotes a conjugated, preferably aromatic system, m is 0 or above, preferably 0 to 3 and particularly preferably 0 or 1, X is a carboxyl, hydroxyl, sulfo and/or amino group, the R radicals represent, independently of one another, any suitable substituents which are chosen so that the dissociation constant for the group X is in the required pH range, and n is an integer from 1 to 5.

X preferably represents a carboxyl or hydroxyl group, and the R radicals overall preferably provide an electron-attracting effect. Examples of suitable R radicals are amino, hydroxyl, optionally $C_{1-10}$-alkyl-substituted amino, nitro and cyano groups, halogen atoms, in particular fluorine or chlorine atoms, alkoxy radicals having up to 10 carbon atoms and ester or sulfonate residues having up to 10 carbon atoms.

The R radicals are chosen so that the X radical is in deprotonated form at a pH above 7 (or is in the form of $-NH_2$ in the case of an amino group) and is protonated in the required pH range, for example at about 6.5. The compound is selected by means of the routine methods described above so that it has a considerably lower cytotoxicity in the deprotonated state than in the protonated state.

The following have proven to be particularly effective
2,4-dihydroxybenzoic acid
4-amino-2-hydroxybenzoic acid
halogenated 2-hydroxybenzoic acid
cinnamic acid their derivatives and
dinitrophenol.

The following are mentioned as example of effective derivatives:
4-acetoxy-2-hydroxybenzoic acid
4-propionic ester 2-hydroxybenzoic acid
4-succinic ester 2-hydroxybenzoic acid
4-glutaric ester 2-hydroxybenzoic acid
4-acetamino-2-acetoxybenzoic acid
2,4-diacetoxybenzoic acid
5-chloro-2-acetoxybenzoic acid
5-bromo-2-acetoxybenzoic acid
3-fluorocinnamic acid
3,4-difluorocinnamic acid Examples of suitable molecular complexes which decompose at pH<7 and release toxic substances are complexes of bile acids or fatty acids and a complex-forming toxic substance, for example nopol (6,6-dimethyl-2-norpinene-2-ethanol).

In a preferred embodiment, 2 or more compounds according to the invention are used in a mixture, or are administered successively in such short time intervals that their effects are suitably complementary.

Figure 1A:
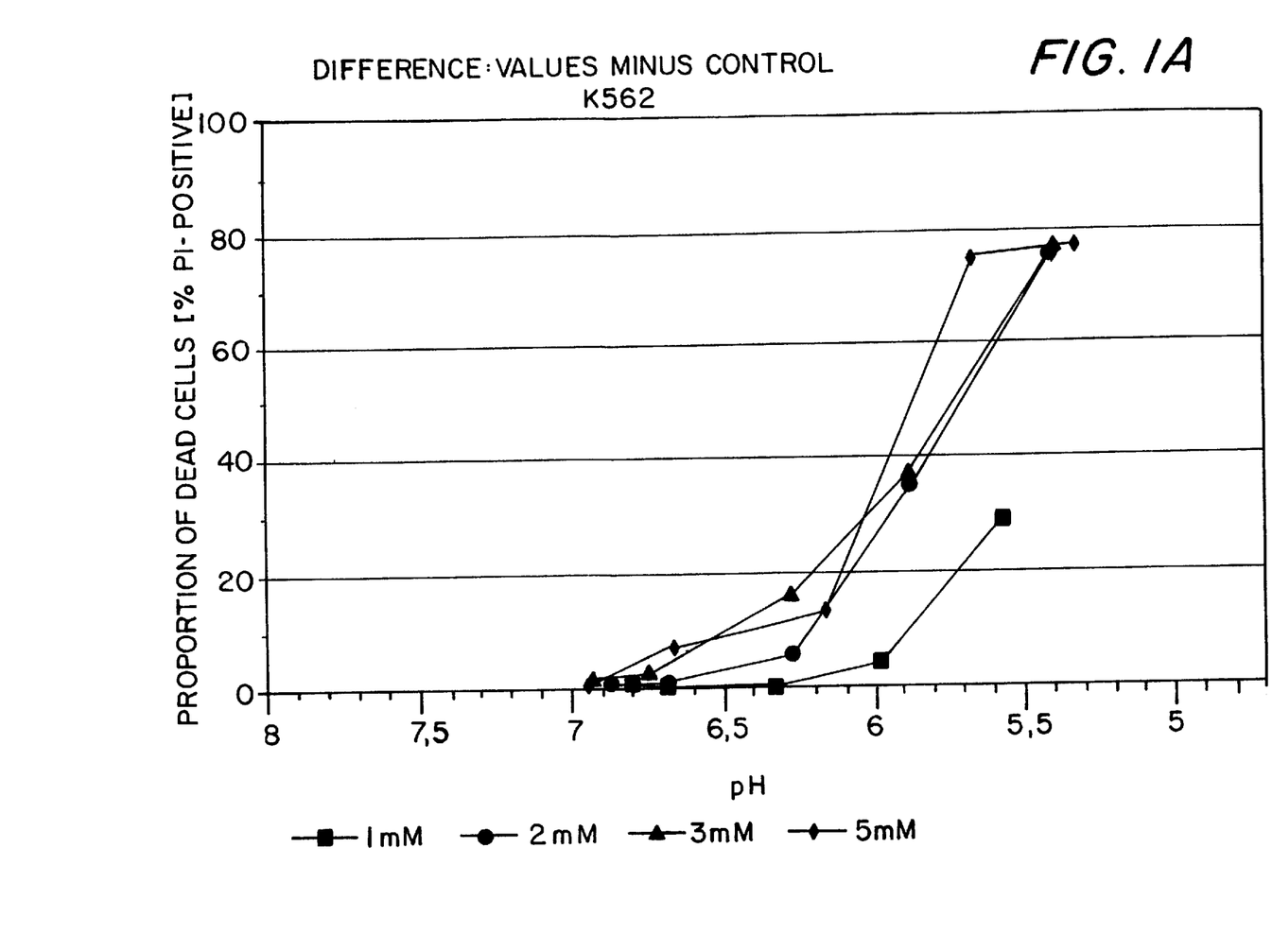
FIG. 1A is a graph which shows the activity of the 4-succinic ester of 2,4-dihydroxybenzoic acid on K-562 cancer cells.
Figure 1B:
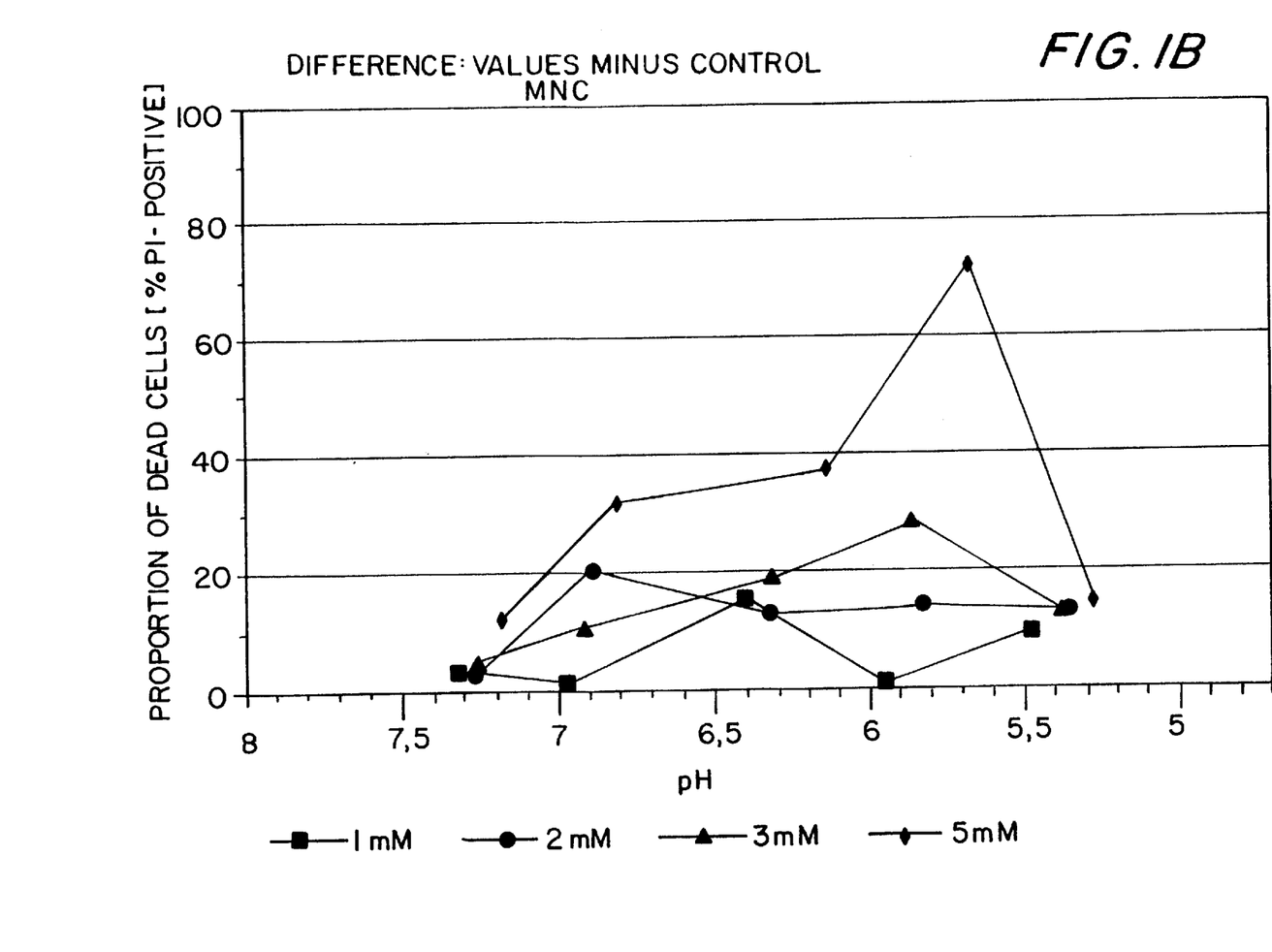
FIG. 1B is a graph which shows the activity of the 4-succinic ester of 2,4-dihydroxybenzoic acid on mononuclear blood cells (MNCs).
Figure 2A:
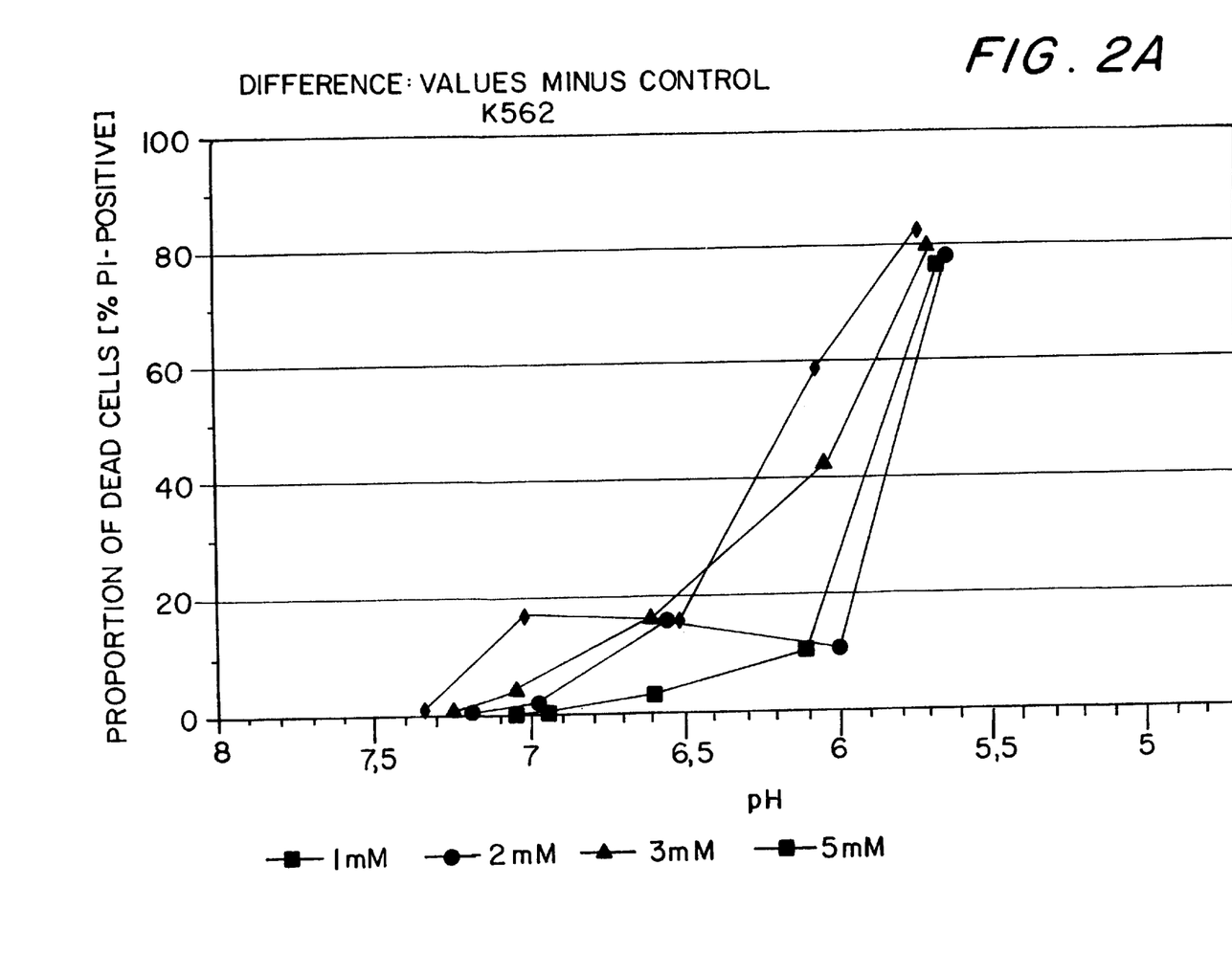
FIG. 2A is a graph which shows the activity of trans-3,4-difluorocinnamic acid on K-562 cancer cells.
Figure 2B:
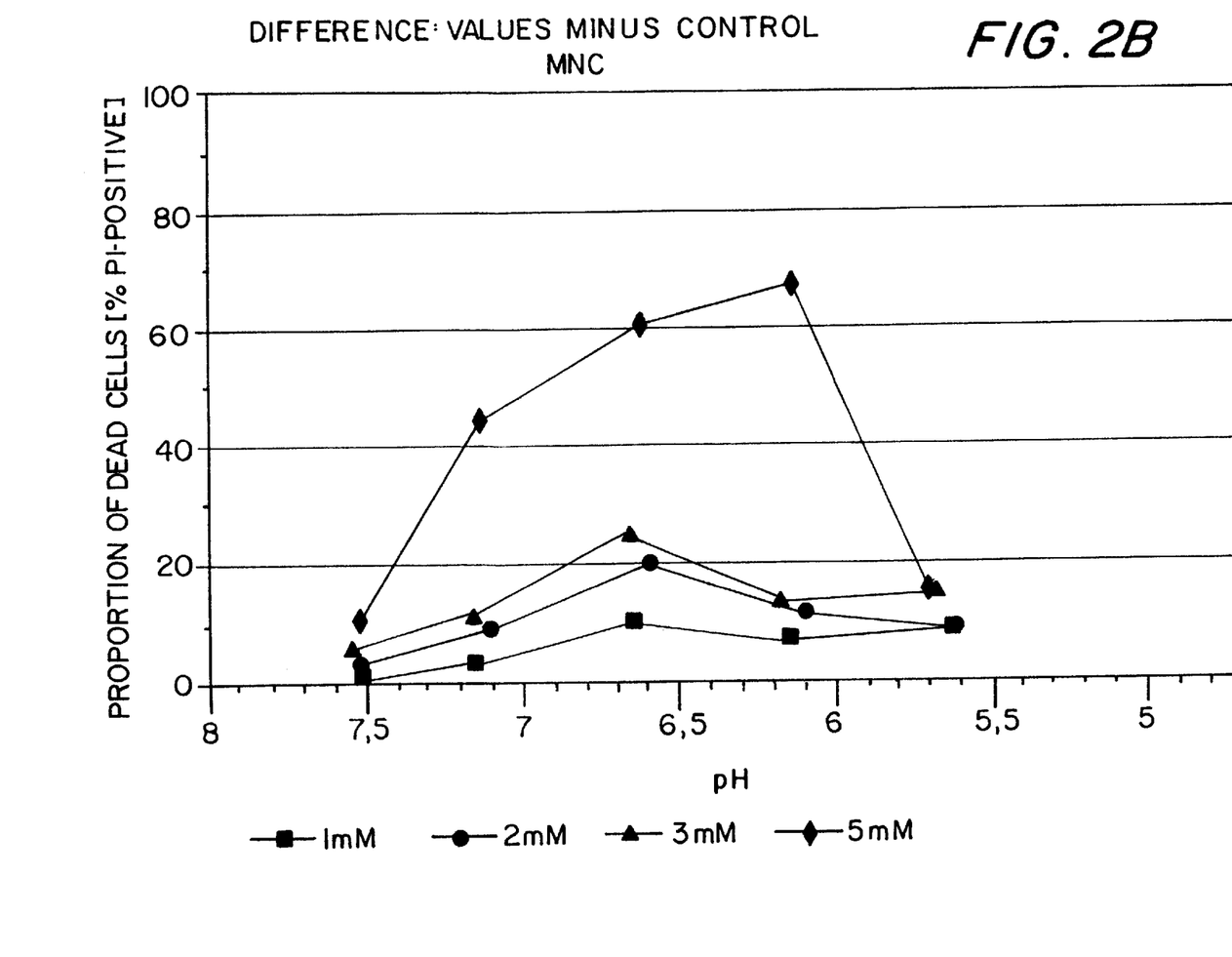
FIG. 2B is a graph which shows the activity of trans-3,4-difluorocinnamic acid on MNCs.

The activity of the 4-succinic ester of 2,4-dihydroxybenzoic acid, of trans-3,4-difluorocinnamic acid and of 2,4-dinitrophenol has been investigated. Used for this purpose were the methods of the FACScan and ELISA techniques described above. FIG. 1A shows the activity of the 4-succinic ester of 2,4-dihydroxybenzoic acid on K-562 cancer cells. It is clear that the toxicity effect has its onset at about pH 6.5 and reaches its maximum at pH 5.7. FIG. 1B shows the mode of action of the same compound on mononuclear blood cells (MNCs). Negligible toxicity is detectable at an extracellular pH in the range from 7.2 to 7.4 as prevails in normal tissue and in blood cells. FIG. 2A depicts the effect of trans-3,4-difluorocinnamic acid on K-562 cells. It is clear that the cytotoxic effect is negligible until the extracellular pH is below 6.5. FIG. 2B depicts the effect of the same compound on MNCs.

Figure 3A:
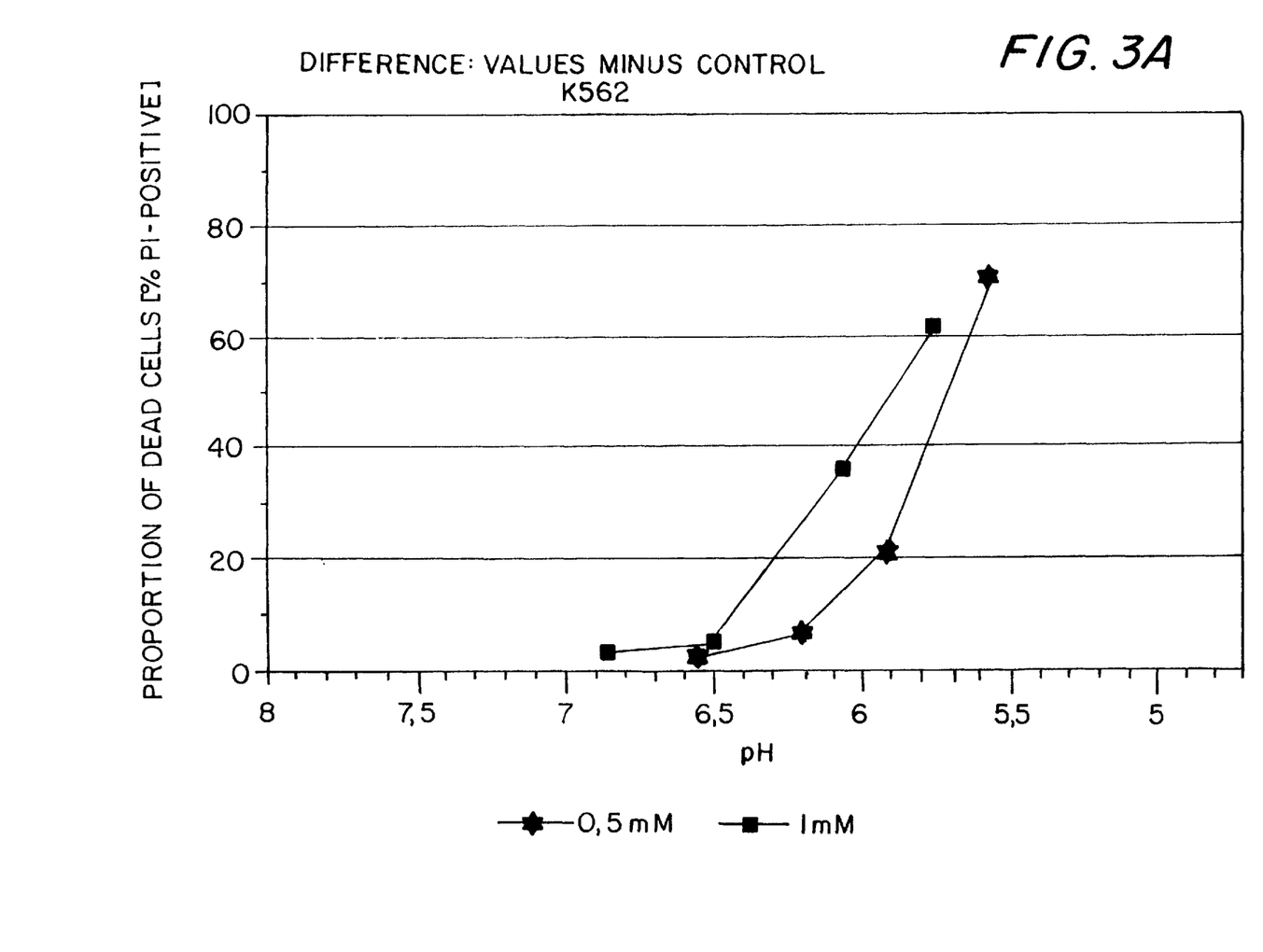
FIG. 3A is a graph which shows the activity of 2,4-dinitrophenol on K-562 cancer cells.
Figure 3B:
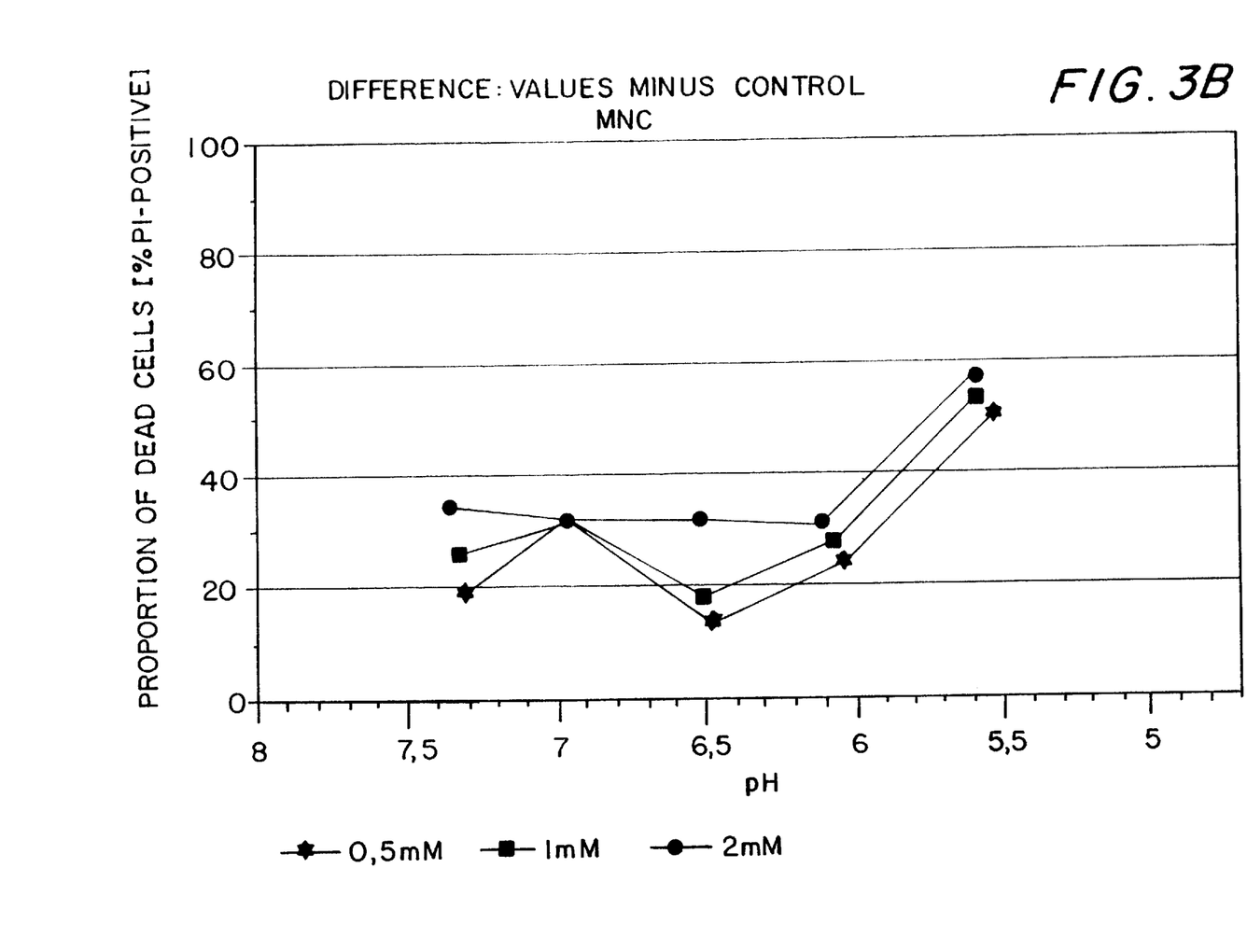
FIG. 3B is a graph which shows the activity of 2,4-dinitrophenol on MNCs.

The corresponding values for 2,4-dinitrophenol are shown in FIGS. 3A and 3B.

It is evident to the skilled person that it is possible by slight changes in the substituents of the abovementioned compounds to shift the pH ranges in which the dissociation equilibrium is located, i.e. in which protonation of the compounds takes place, upwards or downwards.

All the compounds mentioned by way of example show a solubility in water of more than 30 mg/ml.

Figure 4:
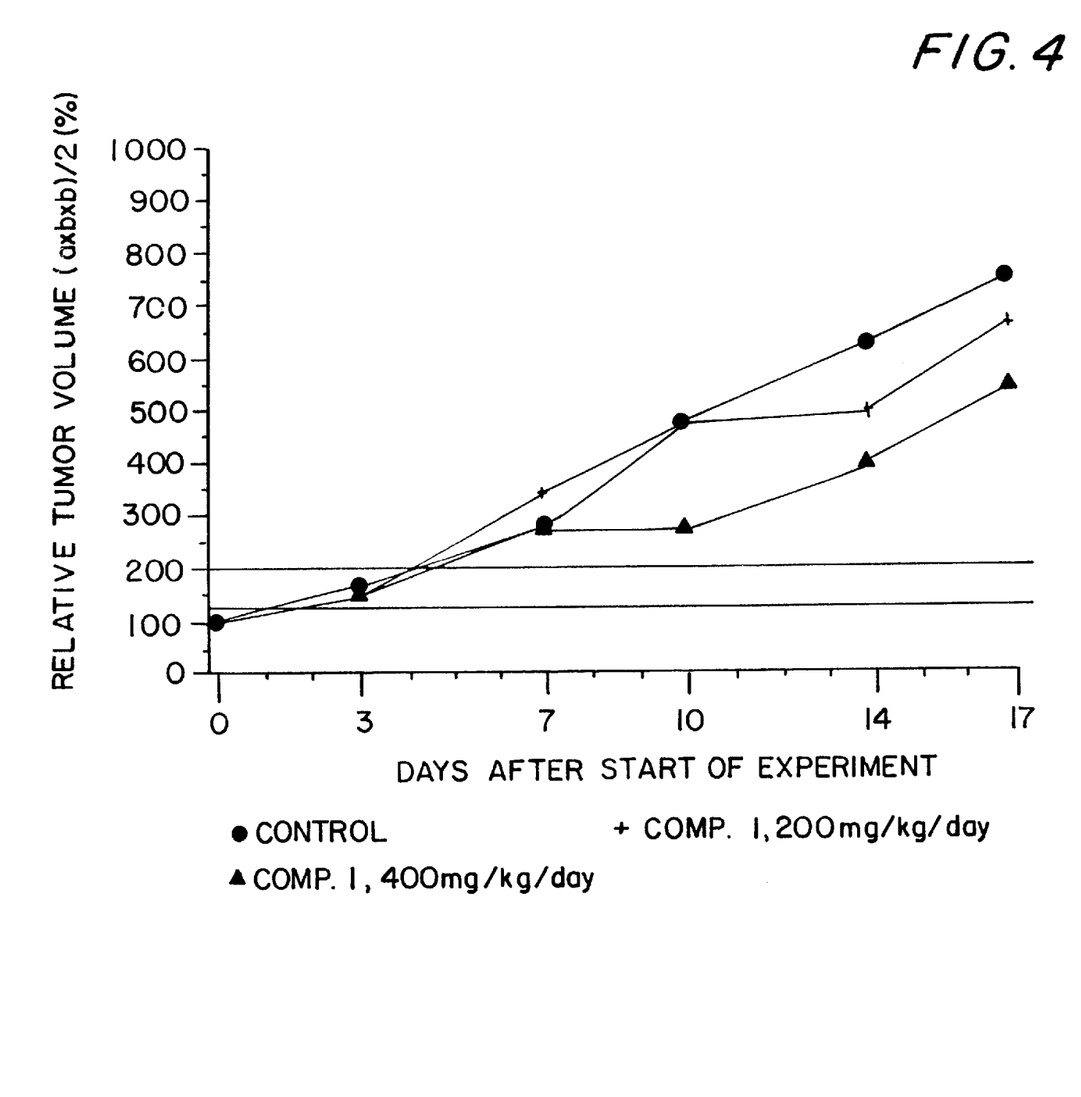
FIG. 4 is a graph which shows the results of an animal experiment which is described in the EXAMPLES set forth below.

The three compounds mentioned above by way of example have likewise been investigated for their in vivo suitability in an animal model. Nude mice are chosen as animal model, into which it is possible to implant various human tumors. This makes it possible to investigate the therapeutic efficacy of the substances under defined reproducible conditions. An animal experiment of this type is documented in FIG. 4. A routine method which is conventional in the prior art and is outlined below is used.

EXAMPLES

A small-cell lung tumor (LXFS 650) whose extra-cellular pH of about 6.9 is close to the physiological pH of 7.2–7.3 is implanted into the nude mice. The therapeutic substance used is, as in FIG. 1, 2,4-di-hydroxybenzoic acid (substance (1)). 3–4 weeks after implantation of the tumor, 15 mice with tumors 5–7 mm in diameter are divided into 3 groups: the first group of 5 serves as control group without therapy, and the substance (1) is injected into the tail vein in a concentration of 200 mg/kg/day in the second group of 5 and in a concentration of 400 mg/kg/day in the third group of 5. In the present experiment, 4 injections into the tail vein were carried out on 4 consecutive days. The damage caused to the veins by this did not permit further injections. The tumor volumes were determined on days 7, 10, 14 and 17. It is evident from FIG. 4 that with a concentration of 400 mg/kg/day there is cessation of growth after day 7 and up to day 10, after which the tumor starts to grow again, because the therapy was not continued further. With 200 mg/kg/day there is onset of a slight effect only on day 10.

The compounds according to the invention can be formulated in a manner known per se to medicinal products for mammals, preferably humans. The compounds according to the invention are present in the medicinal products in a mixture with an organic or inorganic pharmaceutical carrier suitable for enteral or parenteral administrations. Oral administration of the compound according to the invention in tablets, capsules, powders or in liquid form, such as suspensions, in solution, as emulsion or as syrup, is particularly preferred.

In the formulation as tablets there is use of conventional medicinal product carriers such as sodium citrate, lactose, microcrystalline cellulose and starch, lubricants such as anhydrous silica, hydrogenated castor oil, magnesium stearate, sodium lauryl sulfate and talc, and binders such as starch paste, glucose, lactose, gum arabic, mannitol, magnesium trisilicate and talc. If the compounds according to the invention are to be administered as liquids, it is possible to use conventional liquid carrier.

A formulation for injections and infusions as known in the art and described in relevant standard works is likewise preferred.

The dosage form of the compound according to the invention depends very greatly on the specific compound and can be determined by a skilled person on the basis of the condition of the patient to be treated, the severity and nature of the disease to be treated, and possible side effects of the administered substance.

I claim:

1. A medicinal product for the selective control of tumor tissue comprising:
   a) at least two different compounds having a pH below 7 when the compounds are present in a protonated form, said compounds having the formula wherein $R_1$ is hydrogen or a moiety which completes an ester group or an ether group, $R_2$ is independently selected from the group consisting of an amino group, hydroxyl, an ester group, an ether group and a halogen, and n is an integer of 1 to 5; and
   b) a pharmaceutically acceptable inert medicinal product carrier.

2. The product of claim 1, wherein the two different compounds are selected from the group consisting of: (i) 2,4-dihydroxybenzoic acid, 4-amino-2-hydroxybenzoic acid, halogenated 2-hydroxybenzoic acid, and cinnamic acid; (ii) derivatives of the foregoing acids, and (iii) dinitrophenol.

3. The product of claim 2, wherein the derivatives are selected from the group consisting of 4-acetoxy-2-hydroxybenzoic acid, the 4-propionic ester of 2-hydroxybenzoic acid, the 4-succinic ester of 2-hydroxybenzoic acid, the 4-glutaric ester of 2-hydroxybenzoic acid, 4-acetamino-2-acetoxybenzoic acid, 2,4-diacetoxybenzoic acid, 5-chloro-2-acetoxybenzoic acid, 5-bromo-2-acetoxybenzoic acid, 3-fluorocinnamic acid and 3,4-difluorocinnamic acid.

4. The product of claim 1, wherein the two different compounds comprise 2,4-dihydroxybenzoic acid and 4-amino-2-hydroxybenzoic acid.

5. The product of claim 1, wherein the carrier is selected from the group consisting of glucose, lactose, sodium citrate, microcrystalline cellulose, starch, anhydrous silica, hydrogenated castor oil, magnesium stearate, sodium lauryl sulfate, talc, starch paste, gum arabic, mannitol and magnesium trisilicate.

6. The product of claim 1, wherein the carrier comprises glucose.

7. A method for controlling tumor tissue in a host animal which comprises administering to said animal a pharmaceutically effective amount of
   a) at least two different compounds having a pH below 7 when the compounds are present in a protonated form, said compounds having the formula wherein $R_1$ is hydrogen or a moiety which completes an ester group or an ether group, $R_2$ is independently selected from the group consisting of an amino group, hydroxyl, an ester group, an ether group and a halogen, and n is an integer of 1 to 5; and
   b) a pharmaceutically acceptable inert medicinal product carrier.

8. The method of claim 7, wherein the two different compounds are selected from the group consisting of: (i) 2,4-dihydroxybenzoic acid, 4-amino-2-hydroxybenzoic acid, halogenated 2-hydroxybenzoic acid, and cinnamic acid; (ii) derivatives of the foregoing acids, and (iii) dinitrophenol.

9. The method of claim 8, wherein the derivatives are selected from the group consisting of 4-acetoxy-2-hydroxybenzoic acid, the 4-propionic ester of 2-hydroxybenzoic acid, the 4-succinic ester of 2-hydroxybenzoic acid, the 4-glutaric ester of 2-hydroxybenzoic acid, 4-acetamino-2-acetoxybenzoic acid, 2,4-diacetoxybenzoic acid, 5-chloro-2-acetoxybenzoic acid, 5-bromo-2-acetoxybenzoic acid, 3-fluorocinnamic acid and 3,4-difluorocinnamic acid.

10. The method of claim 7, wherein the two different compounds comprise 2,4-dihydroxybenzoic acid and 4-amino-2-hydroxybenzoic acid.

11. The method of claim 7, wherein the carrier is selected from the group consisting of glucose, lactose, sodium citrate, microcrystalline cellulose, starch, anhydrous silica, hydrogenated castor oil, magnesium stearate, sodium lauryl sulfate, talc, starch paste, gum arabic, mannitol and magnesium trisilicate.

12. The method of claim 7, wherein the carrier comprises glucose.

13. The method of claim 7, wherein the two different compounds are administered to the host animal concurrently as two separate compounds, consecutively as two separate compounds and as an admixture of the compounds.

14. A method for controlling tumor tissue in a host animal which comprises administering to said animal a pharmaceutically effective amount of 2,4-dihydroxybenzoic acid.

15. A method for controlling tumor tissue in a host animal which comprises administering to said animal a pharmaceutically effective amount of 4-amino-2-hydroxybenzoic acid.

16. A method for controlling tumor tissue in a host animal which comprises administering to said animal a pharmaceutically effective amount of
   a) a compound having a pH below 7 when the compound is present in a protonated form, said compound having the formula wherein $R_1$ is hydrogen or a moiety which completes an ester group or an ether group, $R_2$ is independently selected from the group consisting of an amino group and a hydroxyl group, and n is an integer of 1 to 5; and
   b) a pharmaceutically acceptable inert medicinal product carrier.

17. The method of claim 16, wherein the compound is selected from the group consisting of 2,4-dihydroxybenzoic acid, 4-amino-2-hydroxybenzoic acid and derivatives thereof.

18. The method of claim 17, wherein the compound comprises 2,4-dihydroxybenzoic acid.

19. The method of claim 17, wherein the compound comprises 4-amino-2-hydroxybenzoic acid.

20. The method of claim 17, wherein the derivatives are selected from the group consisting of 4-acetoxy-2-hydroxybenzoic acid, the 4-propionic ester of 2-hydroxybenzoic acid, the 4-succinic ester of 2-hydroxybenzoic acid, the 4-glutaric ester of 2-hydroxybenzoic acid, 4-acetamino-2-acetoxybenzoic acid, and 2,4-diacetoxybenzoic acid.

21. The method of claim 16, wherein the carrier comprises glucose.

* * * * *